US006603042B2

(12) United States Patent
Brown

(10) Patent No.: US 6,603,042 B2
(45) Date of Patent: Aug. 5, 2003

(54) ANHYDRIDE STABILIZATION

(75) Inventor: Henry C. Brown, Cantonment, FL (US)

(73) Assignee: Huntsman Petrochemical Corporation, Austin, TX (US)

( * ) Notice: Subject to any disclaimer, the term of this patent is extended or adjusted under 35 U.S.C. 154(b) by 0 days.

(21) Appl. No.: 10/223,990

(22) Filed: Aug. 20, 2002

(65) Prior Publication Data

US 2003/0083522 A1 May 1, 2003

Related U.S. Application Data

(62) Division of application No. 09/480,836, filed on Jan. 10, 2000.
(60) Provisional application No. 60/115,770, filed on Jan. 13, 1999.

(51) Int. Cl.[7] .............................................. C07C 53/00

(52) U.S. Cl. ...................................................... 562/887

(58) Field of Search ......................................... 562/887

(56) References Cited

U.S. PATENT DOCUMENTS

| 3,903,117 A | 9/1975 | Stenseth et al. |
| 3,975,408 A | 8/1976 | Boyer et al. |
| 3,985,776 A | 10/1976 | Samans et al. |
| 3,998,854 A | 12/1976 | Samans et al. |
| 4,062,874 A | 12/1977 | Sciaraffa et al. |
| 4,358,600 A | 11/1982 | Kuhlmann et al. |
| 4,446,264 A | 5/1984 | Cottman |
| 4,547,539 A | 10/1985 | Spivac et al. |
| 4,590,301 A | 5/1986 | Lim et al. |
| 5,026,876 A | 6/1991 | Sugawara et al. |
| 5,319,106 A | 6/1994 | Kwon et al. |

FOREIGN PATENT DOCUMENTS

| GB | 1331853 | 9/1970 |
| JP | 41-19405 | 11/1966 |

*Primary Examiner*—Paul J. Killos
(74) *Attorney, Agent, or Firm*—Christopher J. Whewell

(57) ABSTRACT

Disclosed herein are compositions comprising organic anhydrides having a reduced tendency to discolor with time, even when held at elevated temperatures for extended times. The compositions are produced by mixing at least one acid halide and various derivatives of hydroxy carboxylic acids with an anhydride to form a homogenous solution. Also disclosed is a process for preparing the compositions.

10 Claims, No Drawings

ANHYDRIDE STABILIZATION

This Application is a divisional Application of U.S. application Ser. No. 09/480,836 filed on Jan. 10, 2000 and further claims the benefit of U.S. Provisional Application No. 60/115,770 filed Jan. 13, 1999.

FIELD OF THE INVENTION

This invention relates to the color stabilization of organic acid anhydrides. More particularly, the invention relates to the color stabilization of maleic acid anhydride and other anhydrides which are maintained at elevated temperatures for extended periods of time during the course of their production, storage, and handling. The stabilization method and compositions therefor taught herein provide heretofore-unseen synergistic effects which provide for lessened stabilization treatment levels and greater color stability over compositions and methods of prior art.

BACKGROUND

Anhydrides of carboxylic acids are important as raw materials in various industries and such materials are typically available to end users in either solid or molten form, depending upon the particular anhydride and the intended use. Anhydrides of acrylic acid, acetic acid, succinic acid, phthalic acid, and maleic acid are but five examples of such materials, the entire class of which anhydrides is well-known by those skilled in the chemical art.

Most organic acid anhydrides are colorless in appearance immediately after their initial preparation and purification, but are seen to take on or develop a color after being stored at elevated temperatures for extended, or in some cases moderate, periods of time. While the exact reaction mechanism for the development of coloration in such materials varies with the composition in each case, and the inventor hereof does not wish to be bound by any particular theory, it may be surmised that trace quantities of impurities present undergo oxidation, coupling, polymerization, or otherwise react with either themselves or other impurity molecules present, or with the anhydride itself It is also possible that the impurities may function as catalysts for the oxidation of the anhydride or its reaction with itself. Regardless of the mechanism, the development of coloration in such materials is generally indicative of impurities, reactions associated therewith, and/or oxidation.

With the advent of strict quality controls in manufacturing processes, greater attention has in general been paid to the presence of minor impurities in chemical raw materials and other physical attributes such as appearance which were often overlooked in the past. Consistency of quality in raw materials provided to a user has become an increasingly important requisite of the raw material supplier. Therefore, any improvement in the stability of a given raw material is viewed as beneficial to the user of the material and products derived therefrom. Accordingly, a distinct advantage would be gained by the provision of a chemical material or system that may be added to a carboxylic acid anhydride which effectively inhibits chemical reactions occurring within the material when it is maintained at temperatures normally experienced during the usual course of its handling and processing, to the extent that changes in color are minimized over extended periods of time.

The art of stabilization of various organic molecules probably dates back to earlier than the discovery in the 1500's that ethanol was stabilized against oxidation catalyzed by impurities present in its aqueous solution by the burning of a candle of sulfur in a barrel prior to its being filled with wine. Since that time, the number and type of known organic molecules has increased dramatically. The increase in the number of known organic molecules has been attended by an increase in the number of stabilizing additives useful in connection with the various materials, the number and type of which are overly voluminous to be treated herein. However, there has in recent years been a number of publications directed at the stabilization of carboxylic acid anhydrides.

One major carboxylic acid anhydride of particular importance in industry is maleic acid anhydride. This material has found widespread use as a raw material for chemical products useful in a variety of industries, including the manufacture of finished fiberglass products, as a graft copolymer with polyisobutylene for use in forming polyisobutylene-succinic anhydride ("PIBSA") based motor oil and spark-ignition fuel dispersants, and as a comonomer for the manufacture of various multi-functional or highly-engineered copolymers to name but a few.

Maleic acid anhydride may be manufactured starting from a wide variety of raw materials, using processes which have been known for decades. Typically, this material is derived from the catalytic oxidation of a hydrocarbon involving the passing of a gaseous hydrocarbon over a suitable catalyst material in the presence of oxygen. While the number of hydrocarbons from which maleic acid anhydride may be produced is large, most modern production of maleic anhydride is based upon hydrocarbon feed stocks containing four carbon atoms per molecule. The preferred catalyst systems are those which comprise mixed oxides of the elements vanadium and phosphous which are prepared by various proprietary and patented processes wherein the oxidation state of the metal is carefully controlled during catalyst preparation and subsequent annealing or other treatments. Exemplary of processes and catalysts useful in the production of maleic acid anhydride are embodied in the following U.S. Pat. Nos. 3,832,359; 4,111,963; 4,149,992; 4,276,222; 4,253,988; 4,304,723; 4,337,174; 4,359,405; 4,501,907; 4,515,973; 4,528,280; 4,562,268; 4,567,158; 4,632,915; 4,670,415; 4,560,674; 4,855,459; 5,137,860; 5,168,090; 5,185,455; 5,275,996; 5,364,824; 5,617,208; 5,631,387; 5,641,722; 5,734,066; and 5,773,382, the entire contents of which are herein incorporated by reference thereto, as well as patents cited in each as references. As produced from these processes, the maleic anhydride may contain by-products of other organic acids or anhydrides, chromogenic bodies, carbon monoxide, carbon dioxide, and water. Crude maleic anhydride prior to purification can be colored other than water white, and while it can be refined to a substantially color-free material, color generally reappears upon storage as hereinabove described. This is due in part at least to the fact that it is convenient from a manufacturer's standpoint to maintain the temperature at which maleic anhydride is stored in the range of about 60 to 70 degrees centigrade. At such an elevated temperature, many reactions, including colorant-forming reactions between organic molecules occur readily. Therefore, workers have continually sought improved color-stability improvement additive combinations or systems useful in color stabilization of organic acid anhydrides.

In addition to inhibiting reactions which otherwise cause coloration to develop in the anhydride, an additive or system must also not affect the physical properties of the acid anhydride to any extent, and must not in any way interfere with the process(es) or use employed by the end user of the anhydride as a raw material. Therefore, materials or systems which are effective at extremely low concentrations are most desirable.

U.S. Pat. No. 3,975,408 to Boyer et al. discloses and claims an improvement for stabilizing the color of dicarboxylic acids, and especially maleic anhydride, which comprises the addition of a chemical agent selected from halides of transition elements, including titanium, zirconium, cobalt, nickel, ruthenium, vanadium, chromium, manganese, mercury, silicon, phosphorous, bismuth, antimony, lead cerium, and sulfur. The level of treatment is between about 0.01 to 1,000 parts per million by weight, based on the total weight of the anhydride.

U.S. Pat. No. 3,985,776 to Samans et al. teaches the stabilization of maleic anhydride through the use of stannous compounds such as stannous chloride and stannous salts of aliphatic monocarboxylic acids. The level of treatment is between about 1 and 2,000 parts per million based on the weight of the maleic anhydride.

U.S. Pat. No. 3,998,854 to Samans et al. sets forth the use of trithiophosphites as stability additives for use in color-stabilization of maleic anhydride, particularly, the trialkyl derivatives of phosphorous acid which are disclosed as effective in this regard at concentrations between 1 and 2,000 parts per million ("ppm") based on the total weight of the maleic anhydride.

U.S. Pat. No. 4,062,874 to Schiaraffa et al. teaches the use of the stabilization of maleic acid anhydride using 4,4'-di(hydroxyphenyl)alkanes or with 4-alkylphenols. The concentration level is disclosed to be between 1 and 200 ppm, based on total anhydride weight.

U.S. Pat. No. 4,358,600 to Kuhlmann et al discloses a process for producing maleic anhydride having an improved color property after aging which comprises the metal-chloride catalyzed polymerization of the color bodies present in the crude maleic anhydride prior to its distillation in the rectification process.

U.S. Pat. No. 4,446,264 to Cottman sets forth mixtures of antioxidants produced from reacting maleic anhydride, acid, or esters thereof with thiols, claimed to exhibit synergy when combined with phenolic anti-oxidants, and useful in stabilizing polymers, lubricants, and oils.

U.S. Pat. No. 4,547,539 to Spivac et al. teaches the use of substituted succinic anhydrides as stabilizers for polyolefins and rubbers.

U.S. Pat. No. 4,590,301 to Lim et al. discloses the use of a family of substituted phenols and Quinonoid compounds as being useful as polymerization inhibitors for acrylic and other monomers.

U.S. Pat. No. 5,319,106 to Kwon et al. discloses a process for removing residual acrylic acid from crude maleic anhydride prior to the rectification of the maleic anhydride, using phenothiazine as an inhibitor.

While each of the above reference patents, each of which (including patents referenced in each) are herein incorporated by reference thereto, possess varying degrees of desirable characteristics for prevention of color formation in organic acid anhydrides held at temperatures greater than ambient for sustained periods, each has one or more drawbacks associated with it, including relatively high treatment levels, relatively high cost, cumbersome in use, toxicity, etc.

In order to evaluate samples of organic acid anhydrides for color stability, a sample aliquot is placed in a suitable container, such as in a beaker, test tube, or similar vessel having a convenient capacity, usually between about 50 and 250 milliliters with the amount of sample used being in the range of about 25 to 100 milliliters. The vessel and its contents are placed in a location of constant temperature for a prescribed amount of time. One preferred method involves the use of a block of a metallic element or a metallic alloy, into which has been drilled a plurality of holes each having a diameter which is just slightly larger than the outer diameter of the vessel containing the sample that is to be evaluated, to a depth of at least the level of the anhydride in the vessel in which it is contained. The block is brought to the temperature at which it is desired to expose the sample by either external means or, more preferably, an internal heating means such as a resistance coil. Another preferred method involves placing the vessel containing the sample to be tested into a stirred bath of constant temperature, such as an oil bath, for a prescribed time. Following the heat stress treatment, the color of the sample is observed and compared to either the untreated sample, or to a standard chart or the like, and a numerical value is recorded.

At present there is no universally accepted IUPAC or equivalent standard of temperature/time profile under which to subject a given sample of organic anhydride for evaluative purposes relating to color stability. Rather, different countries and regions have adopted such profiles as they individually have seen as being most fit for themselves, based largely on historical empirical observations. For example, in the United States and in parts of Europe samples of maleic anhydride are tested for color stability at 140 degrees centigrade for a two hour time period, with specifications for acceptable color related to the APHA color. Manufacturers in most parts of Asia, however, prefer to expose the anhydride to a temperature in the range of about 180 to 185 degrees centigrade for a time period between about 13 and 15 minutes. It is true in general that the samples of industrially-produced organic acid anhydrides tend to change color more readily under conditions of higher temperatures than when maintained at lower temperatures. In this regard, the higher temperature test may provide quicker results.

Various scales for measurement of the color of organic liquids have been devised over the years. The American Public Health Association (hereinafter "APHA") has developed a color-matching test which some producers and consumers find convenient. This scale is well-known in the art, and is often used for reporting how far off-color various chemical materials are. The standards are used by simply comparing a liquid's color to a series of yellow or yellow-brown standards. The results of the test are reported in units known as "Hazen" units, the use of which is well-known in various arts. Unless otherwise specified, all data reported herein for the color of anhydride materials shall be in Hazen values.

SUMMARY OF THE INVENTION

The present invention relates to an organic acid anhydride product having a high degree of discoloration resistance. An organic acid anhydride product according to the invention is formed from the admixture of an organic acid anhydride with additives comprising an acid halide of a carboxylic acid, and a derivative of a hydroxy carboxylic acid having, in a preferred embodiment, between two and sixteen carbon atoms per molecule. The derivative of the hydroxy carboxylic acid may be the acid itself, or salts, esters, or other derivatives of the acid. In another embodiment of the invention, a combination including more than one derivative of a hydroxy carboxylic acid may also be used. Additionally, a transition metal salt which possesses either an organic or an inorganic anion, or a plurality of salts of different transition metals having inorganic and/or organic anions may be optionally included in an anhydride stabilized in accordance with these embodiments according to the invention.

The invention also relates to a process for producing the stabilized organic acid anhydride compositions which includes the admixture of the various components of the composition into an organic anhydride. The anhydride product that results from the admixture is particularly stable with respect to color changes over time, when stored at ambient or elevated temperatures for extended periods. The amount of additives added to the anhydride is in the parts per million range.

To practice the instant invention, one provides an organic acid anhydride, and then adds the synergistic additives herein taught to the anhydride in the prescribed amounts. The anhydride is preferably in the molten or liquid state to promote uniform mixing, although this is not absolutely necessary. For example, in the case of anhydrides that are solid at ambient temperatures, the solid pellets, chunks, briquettes, or other solid mass of the anhydride may be dusted by a composition comprising the additives taught herein in an effective color-stabilizing amount. Since nearly all consumers of anhydrides normally solid at ambient temperatures render the materials to the liquid state prior to their employment in their end use, a dust coating would be readily incorporated into the mass of the molten substance upon its melting.

Although the compositions taught in the instant invention are described with respect to their ability to inhibit color-forming reactions in organic acid anhydrides, it may be readily anticipated that the compositions may function equally well in other materials and systems where similar products are produced from like starting materials, or are exposed to like storage conditions. Such other materials may include all organic molecules known by those skilled in the art of organic chemistry to undergo an undesirable degree of discoloration.

Organic anhydrides which may be stabilized according to the invention include without limitation those anhydrides which yield organic acids having between 1 and 16 carbon atoms per molecule upon hydrolysis of which acetic anhydride, succinic anhydride, maleic anhydride, and phthalic anhydride are exemplary.

DETAILED DESCRIPTION

The additive system used to provide the final compositions according to this invention comprises an acid halide of a carboxylic acid and a metal salt of a hydroxy carboxylic acid, which are added at parts-per-million levels to an organic acid anhydride product, either alone or in combination with other additives taught herein. In a preferred form of the invention the metal salt is a transition metal salt, and the acid halide and transition metal salt are preferably added to the anhydride when the anhydride is in the liquid state.

Organic acid anhydrides of commerce are typically purified by distillation using means known to those skilled in the art. To illustrate the proneness of freshly distilled, neat anhydride to color changes, samples of freshly distilled, neat maleic acid anhydride ("MAA") were acquired from a commercial production plant and stored at 65 degrees Centigrade for 5 days. The APHA color was determined using a "Lovibond Tintometer model PFX 990", available from HF Scientific, Inc. at 3170 Metro Parkway, Fort Meyers, Fla., which unit was used for gathering of all other Hazen value data set forth in the various tables herein. Samples of the same material were also subjected to heat stress test conditions of 140° C. for 2 hours and 182° C. for 1 hour. Table I lists the data for the material as stored, and after being subjected to the aforementioned heat stress conditions. From these data it is evident that neat MAA is very susceptible to color changes even at moderate temperatures, and is extremely susceptible to color changes at higher temperatures. The same can be shown to be true for other organic acids and anhydrides, especially those that are solids at ambient temperatures.

TABLE I

| Heat stress test results for neat MAA (in Hazen units) | | |
|---|---|---|
| As stored, 65° C., 5 days | 140° C., 2 hours | 182° C., 1 hour |
| 10 | 140 | >500 |

The Acid Halide Component

One group of additives which has been explored for use in preventing discoloration of commercially-produced acid anhydrides are the acid halides of carboxylic acids. Acid halides of carboxylic acids, (including aryl and acyl halides), are well known in the art, and are described in high-quality college-level organic chemistry textbooks, an example being "Introduction to Organic Chemistry", by Streitweiser and Heathcock, $2^{nd}$ ed. MacMillan Publishing Company, New York (1981), the entire contents of which are herein incorporated by reference, on pages 517, et seq. Acid halides are the reaction product between a carboxylic acid (carboxylic acids are sometimes also referred to as "organic acids" by those skilled in the art) and a suitable halogenating agent such as the trichloride and pentabromide of phosphorous, or the thionyl halides such as thionyl chloride and thionyl bromide. In the formation of acid halides, the hydroxy group of a carboxylic acid function is replaced by a halogen atom, usually chlorine or bromine. Accordingly, for purposes of the instant specification and the appended claims, the words "acid halide" means the reaction product of a carboxylic acid having at least one carboxyl function with a halogenating agent, including, but not limited to phosphorous pentachloride or thionyl chloride, such that the hydroxy group of the carboxylic acid function of a carboxylic carbon atom is replaced by a halogen atom, such as a chlorine atom. These and other halogenating agents like N-bromo succinimide are known to those skilled in the art, and for purposes of this specification and the appended claims a halogenating agent means a molecule which is capable of providing a halogen atom which can be incorporated into other different molecules, as in the case of the formation of acid halides. Acid halides yield a carboxylic acid and a hydrogen halide upon hydrolysis. Preferably, the acid halide used is one which yields between 1 and 25 carbon atoms per molecule (including every integral number of carbon atoms therebetween) upon hydrolysis. Typical acid halides include formyl chloride, acetyl chloride, phthaloyl chloride, succinyl chloride, and maleyl chloride.

Acid halides suitable for use in the instant invention include, but are not limited to: all known acid halides including those set forth in U.S. Pat. No. 3,903,117 (the entire contents of which are herein incorporated by reference (including acyl halides of straight-chain or branched carboxylic acids having between 2 and 20 carbon atoms per molecule such as acetyl chloride; propionyl chloride; butyroyl chloride; etc. Acyl halides derived from di-acids are also useful in this invention, including without limitation, as examples: oxalyl chloride; oxalyl bromide; malonyl chloride; succinyl chloride; succinyl bromide; maleyl monochloride; maleyl dichloride; maleyl bromide; phthaloyl chloride; phthaloyl bromide; benzoyl chloride; terephthaloyl chloride;

salicylyl bromide; etc. For di-carboxylic acids, it is not necessary that all carboxylic acid functions be replaced by halogen atoms. A mono-halogenated derivative of a di-acid, mono- or di-halogenated derivative of a tri-acid, etc., are herein indicated as being useful in this regard and fall within the definition of acid halide for purposes of this specification and the appended claims. All known aryl halides are also useful as acid halides. The effectiveness of phthaloyl chloride in this employ is illustrated by the data in Table II, in which are set forth color stability test results conducted on two samples of MAA containing phthaloyl chloride at a level of about 9 ppm:

TABLE II

Hazen values for MAA treated with phthaloyl chloride as thermal aging stabilizer

| Sample Number | phthaloyl chloride (ppm) | Initial APHA | 140° C. 2 hours | 182° C. 1 hour |
|---|---|---|---|---|
| 1 | 9.0 | 8 | 16 | 80 |
| 2 | 9.0 | 8 | 12 | 38 |

It is clear from the Hazen values for samples 1 and 2 that the presence of 9.0 ppm of phthaloyl chloride significantly inhibits the darkening of MAA under the test conditions employed. However, a large degree of darkening is still evident in the sample that was subjected to the 182° C. test.

It has been unexpectedly discovered by exhaustive experimentation that when certain combinations of chemical compounds are added to MAA which contains an acid halide such as phthaloyl chloride, a synergistic effect is produced which reduces the tendency of the MAA to discolor to a greater degree than when any of the compounds alone are added to the MAA. The compounds so discovered as being useful in this regard are derivatives of hydroxy carboxylic acids, including especially metallic salts and esters thereof Therefore, owing to the synergy discovered, only small amounts of acid halides are necessary to be added to an organic anhydride that is to be color-stabilized in accordance with this invention. Typically, the amount of acid halide used in forming a composition according to the invention is between 0.000001% and 1.000000% including every incremental 0.000001% therebetween, based upon the total weight of the anhydride product. In general terms, the amount of acid halide present in a product made in accordance with the invention will be an effective amount for inhibiting color changes in the anhydride product when said product is subjected to temperatures greater than at least 10 degrees centigrade greater than the melting point of the anhydride.

The Hydroxy Carboxylic Acids and Their Derivatives

The term "hydroxy carboxylic acid" as used in the instant specification and the appended claims means an organic compound including one or more carboxylic acid functions in its molecular structure, and at least one hydroxy group bonded to a carbon atom other than that of a carboxylic acid carbon in the molecular structure. Such compounds are well-known in the art, and include, without limitation such acids as: gluconic acid; glucoheptonic acid; hydroxyacetic acid; hydroxy propionic (a.k.a. "propanoic") acid; hydroxybutyric acid; glycolic acid; 2-hydroxy propanoic acid; 3-hydroxy propionic acid; 2,3 di-hydroxy propionic acid; 3,4 di-hydroxy glutaric acid; 3,4,5 tri-hydroxy glutaric acid; the uronic acids such as D-Glucuronic acid; the aldonic (glyconic) acids; the aldaric (glycaric) acids; and the ketoaldonic acids. Many members of this broad general class of materials may be derived from carbohydrates, such as glucoses, glyceraldehydes, enoses, trioses, tetroses, pentoses, hexoses, etc., all provided that they possess an alcohol or aldehyde function capable of being oxidized to a carboxylic acid by means known to those skilled in the art, without regard to the presence of other functional groups. Also included within this definition are the polyhydroxy carboxylic acids, i.e., carboxylic acids having more than one hydroxy group present in the molecule. Also embraced by this definition and suitable as additives within the context of the present invention are the hydroxy carboxylic acids that are aromatic in character, and those hydroxy carboxylic acids having more than one carboxylic acid function per molecule. Molecules comprising such acids or their derivatives include:

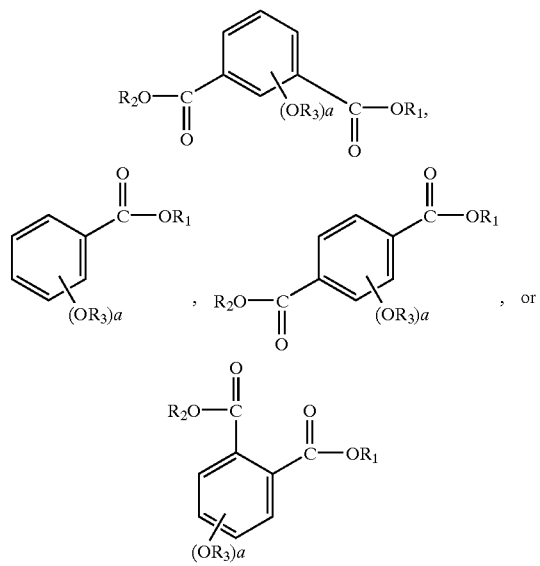

wherein $R_1$, $R_2$ are each independently selected from the group consisting of: a cationic species, hydrogen; $C_1$ through $C_{12}$ straight-chain, branched, or cyclic alkyl; $C_1$ through $C_{12}$ straight-chain, branched, or cyclic alkenyl; substituted or unsubstituted phenyl; and $R_3$ is selected from the group consisting of hydrogen; $C_1$ through $C_{12}$ straight-chain or branched alkyl; substituted or unsubstituted phenyl; and a is any integer between 1 and 4, and all isomers thereof, whether position, structural, or stereoisomers. Other substituents known to those skilled in the chemical arts may be appended to the aromatic ring.

For purposes of this specification and the appended claims, the words "derivative of a hydroxy carboxylic acid" means any organic compound that is a condensation product, ionic species, ester, coordination compound, ether, aldol, aldehyde, lactone, acetal, hemiacetal, ketal, adduct, graft copolymer, etc. or that may be derived directly from a hydroxy carboxylic acid. Common derivatives of hydroxy carboxylic acids include without limitation esters, metallic salts, amines (via reduction of a nitrile), amides, imides, alcohols (as from reduction), nitriles (via nucleophilic substitution of an alkyl halide derived from the parent acid), alkyl halides, and ammonium salts, and other derivatives of hydroxy carboxylic acids known to those skilled in the art of organic chemistry fall within this definition.

"Salts" according to this invention mean the types of compounds normally regarded by chemists as being salts, including metallic salts, ammonium salts, phosphonium salts, or any other ionic species (including all known complexes and complex ions) capable of donating electrical charge to a molecule effectively to maintain charge balance. Salts also include those salts formed not only by reaction of a proton of the carboxylic function of the organic acid, but those of the proton from a hydroxy group, when chemically feasible, as in the case of when a phenolic proton is present on an aromatic ring, the reactivity of which is well known to those skilled in the art. That is, it is known that the acidic proton on phenol or its known derivatives undergoes reaction quite readily with an alkaline sodium-bearing substance to form a sodium phenolate. A suitable derivative of a hydroxy carboxylic acid (for exemplary purposes only, and not delimitive of this invention) for use in this invention would be a mono, di- or tri-sodium (or any other metallic species, including any of the transition metals, lanthanides, or actinides) salt of ethyl gallate. In other cases, such as where an electron withdrawing group or atom, such as a halogen atom, is bonded to a carbon atom adjacent to a carbon atom that bears a hydroxy group, the proton of the hydroxy group may have sufficient acidity to provide a site for salt formation. Accordingly, salts of hydroxy carboxylic acids formed from the reaction of an aromatic hydroxy proton are included within the definition of derivative of hydroxy carboxylic acid for purposes of this specification and the claims appended hereto. One exemplary compound, without limitation, would be the sodium salt of 2-chloro, 3-hydorxy, benzyl proprionate. When a salt of a derivative of a hydroxy carboxylic acid is employed to form a product according to the invention, such a salt would be present in an amount between about 0.000001% and 1.000000%, including every 0.000001% increment therebetween, based upon the total weight of the anhydride product. Typical salts useful according to the invention would include metal salts of a hydroxy carboxylic acid, including the copper, zinc, nickel, tin, iron, cobalt, and aluminum salts thereof.

The word "metal", as used in this specification and the appended claims means all of the transition metals and includes all alkali metals, all alkaline earths, all group III metals, all of the lanthanides, and all of the actinides, as such elements are generally recognized as metals by those skilled in the chemical arts.

In general terms, a derivative of a hydroxy carboxylic acid that is used in producing a product according to the invention will be derived from a hydroxy carboxylic acid that comprises between 2 and 25 carbon atoms per molecule, including every integral number of carbon atoms therebetween. The amount of each selected derivative of a hydroxy carboxylic acid used to form a product made according to the invention will be an effective amount for inhibiting color changes in the anhydride product when said product is subjected to temperatures greater than at least 10 degrees centigrade greater than the melting point of the anhydride. The amount of each selected derivative of a hydroxy carboxylic acid used in forming a composition according to the invention (whether one desires to employ a single, two, or even three derivatives of a hydroxy carboxylic acid) is preferably between 0.000001% and 1.000000% including every incremental 0.000001% therebetween, based upon the total weight of the anhydride product. More preferably, this amount is between 0.10 parts per million and 5.00 parts per million, and including every hundredth part per million therebetween.

When it is desired to employ more than a single derivative of a hydroxy carboxylic acid in forming an anhydride product according to the invention, each derivative is preferably present in amounts effective to provide an anhydride product having a Hazen value less than 50 when subjected to a temperature of 182° C. for one hour. Typically, such an amount is between about 100 parts per billion and 1000 parts per million, including every incremental part per billion therebetween based upon the total weight of the anhydride product. More preferably, however, such an amount is less than 5.0 parts per million, with 0.5 parts per million being more preferable still.

The Synergistic Compositions

To illustrate the effects discovered, copper (II) gluconate and copper (II) 3,5-di-isopropyl salicylate ("3,5-DIPS") are each added to MAA in combination with phthaloyl chloride, in amounts as set forth in Table III. From the data for samples 3 and 4 it can be seen that each of these compounds when used alone exhibit a trifling ability to inhibit the darkening of MAA under the test conditions. However, when combined with phthaloyl chloride, as in samples 5, 6, 7, and 8, the synergistic effects of the combination become clear. The exceptionally low level of treatment necessary to achieve the discoloration inhibition exhibited by samples 5 through 8 is so remarkable as to make this combination particularly advantageous over heretofore available systems from the perspectives of both manufacturers and users of organic acid anhydrides, especially MAA.

TABLE III

Hazen values for MAA containing various additives subjected to various temperature / time profiles

| Sample Number | phthaloyl chloride (ppm) | Cu(II) Gluconate (ppm) | Cu(II) 3,5-DIPS (ppm) | Initial APHA | 140° C. 2 hours | 182° C. 30 min. | 182° C. 1 hour |
|---|---|---|---|---|---|---|---|
| 1 | 9.0 | — | — | 8 | 16 | — | 80 |
| 2 | 9.0 | — | — | 8 | 12 | — | 38 |
| 3 | — | 1.0 | — | 8 | >60 | 110 | 250 |
| 4 | — | — | 1.0 | 8 | 22 | 45 | 100 |
| 5 | 9.0 | 1.0 | — | 8 | 22 | 22 | 32 |
| 6 | 9.0 | 1.0 | — | 8 | 18 | 22 | 28 |
| 7 | 9.0 | — | 1.0 | 8 | 18 | 20 | 30 |
| 8 | 9.0 | — | 1.0 | 8 | 16 | 18 | 26 |

A preferred method of producing stabilized anhydride compositions according to the invention involves the addition of the transition metal salt and acid halide to the acid anhydride while the anhydride is in the molten state. In the case of maleic anhydride, the preferred temperature at which the MAA is maintained during the addition is between about its melting point and 50 degrees centigrade above its melting point, with 15 degrees centigrade above its melting point being most preferable. This temperature of about 15 degrees above its melting point is applicable to other anhydrides as well. While there is no preferred order of addition of the components of the instant stabilization system, it is preferred that powdered additive components not be permitted to form clumps in the melt. Towards this end, the materials are most preferred when existing in a fine powdered form and are evenly dispersed throughout the liquid anhydride to which they are added, such as through the use of a sifter similar in operating principle to those used to sift flower for baking.

For preparation of samples 3 through 8, the copper salts and the acid halide were added directly to the molten MAA at 65° C., followed by sufficient mixing to ensure homogeneity of the resultant solution. For samples in Table III containing both phthaloyl chloride and a copper salt, the phthaloyl chloride was added first. However, no noticeable difference in discoloration inhibition is observed in final samples of stabilized MAA when the copper salts are added prior to the phthaloyl chloride.

From a commercial economics standpoint, it is desirous to utilize only that necessary amount of a particular additive or additive combination for achieving a desired result, with any excess being generally regarded as wasteful. In observance of this general rule, it was desired to determine the optimum amount of cupric gluconate useful towards color-stabilization of MAA that contains 9.0 ppm of phthaloyl chloride. Therefore, two separate samples of MAA (samples 9 and 13) each containing 9.0 ppm of phthaloyl chloride were treated with different levels of cupric gluconate as shown in Table IV, below, which also sets forth test results of thermal color-stability tests:

TABLE IV test results pointing towards the optimum level of Cupric gluconate in MAA according to the invention.

| Sample Number | phthaloyl chloride (ppm) | Cu(II) gluconate (ppm) | Initial APHA | 140° C. 2 hours | 182° C. 1 hour |
|---|---|---|---|---|---|
| 9 | 9.0 | — | 6 | 12 | 170 |
| 10 | 9.0 | 1.0 | 24 | 24 | 32 |
| 11 | 9.0 | 0.5 | 16 | 16 | 28 |
| 12 | 9.0 | 0.25 | 12 | 14 | 24 |
| 13 | 9.0 | — | 6 | 10 | 120 |
| 14 | 9.0 | 1.0 | 20 | 22 | 32 |
| 15 | 9.0 | 0.5 | 14 | 18 | 30 |
| 16 | 9.0 | 0.25 | 10 | 14 | 22 |

Samples 10, 11, and 12 were made from a larger portion of sample 9, which had come from a different lot than sample 13, from which samples 14, 15, and 16 were prepared. From these data, it is seen that an increased degree of color stability is attendant with the lesser quantities of cupric gluconate added over the range employed. That is, lower Hazen values for the 182° C. test were observed in samples having the lowest amounts of added gluconate. This result, when combined with the results obtained for samples containing no cupric gluconate, proves that the effect on color stability conferred by the presence of both phthaloyl chloride and cupric gluconate are not additive as one would expect, but rather are synergistic.

Another aspect of the instant invention is that the presence of aromatic acids and/or their esters (including those which are derivatives of hydroxy carboxylic acids) may act in further synergy with the phthaloyl chloride and cupric gluconate combination towards inhibition of the darkening of organic acid anhydrides upon their being maintained at elevated temperatures for extended times. Towards this end, the ester formed from gallic acid and n-propanol (n-propyl gallate), has been found especially beneficial. To illustrate, to a fresh sample of MAA was added 9 ppm phthaloyl chloride, and the results of heat stress tests run on the sample is reported in Table V as was done in Table IV for sample 9. (It may be noted that the test result data for this material differs slightly from those reported in the previous tables for MAA containing 9.0 ppm phthaloyl chloride. This is a normal evidence of minor variations in the composition of the neat material owing to typical variations in the manufacturing process, and such individual "blank" samples (such as samples 9,13, and 17) are used herein to minimize or eliminate bias in the results that are based upon normal manufacturing variations).

TABLE V effect of n-propyl gallate ("n-PG") on color change inhibition of molten MAA stabilized with phthaloyl chloride / cupric gluconate combination.

| Sample Number | phthaloyl chloride (ppm) | Cu(II) gluconate (ppm) | n-PG (ppm) | Initial APHA | 140° C. 2 hours | 182° C. 1 hour |
|---|---|---|---|---|---|---|
| 17 | 9.0 | — | — | 8 | 16 | 110 |
| 18 | 9.0 | 0.5 | — | 10 | 14 | 26 |
| 19 | 9.0 | 0.25 | — | 10 | 16 | 26 |
| 20 | 9.0 | 0.5 | 1.0 | 8 | 14 | 20 |
| 21 | 9.0 | 0.25 | 0.5 | 8 | 14 | 22 |

Addition of the amounts of propyl gallate listed in table V is seen to further inhibit the tendency of the MAA to darken, especially under the more severe test conditions of 182° C. for 1 hour. According to a preferred form of the invention, maleic anhydride samples which contain n-propyl gallate, Cu(II) gluconate and phthaloyl chloride retain their ability to inhibit discoloration in the molten anhydride, even when such maleic anhydride samples which contain these additives are stored in the molten state for extended periods of time of at least 4 weeks.

Other esters as described herein are indicated as being useful in the stead of the n-propyl gallate as set forth above, including esters which are derived from alcohols having between 2 and 20 carbon atoms per molecule, including every integral number of carbon atoms therebetween. Preferably such esters are present in an anhydride product produced in accordance with the invention in an amount between 0.001 parts per million and 10.000 parts per million, and including every thousandth part per million increment therebetween, based upon the total weight of the anhydride product. More preferably, the amount is between 0.100 parts per million and 5.000 parts per million, and including every thousandth part per million increment therebetween, based upon the total weight of the anhydride product.

Another compound that has been discovered to be of benefit as a component of a synergistic mixture according to this invention is cupric 3,5-di-isopropyl salicylate ("Cu(II) 3,5-DIPS"). Formulations containing MAA, phthaloyl chloride, cupric gluconate, and this derivative of a hydroxy carboxylic acid were prepared and tested as before. The compositions of these formulations as well as test results obtained thereon are set forth below in Table VI, thus:

TABLE VI test results pointing towards the optimum level of additives in various systems

| Sample No. | phthaloyl chloride (ppm) | Cu(II) gluconate (ppm) | Cu(II) 3,5-DIPS (ppm) | n-PG (ppm) | Initial APHA | 140° C. 2 hours | 182° C. 1 hour |
|---|---|---|---|---|---|---|---|
| 22 | 9.0 | — | — | — | 8/10/12 | 12/16/16 | 400/350/120 |
| 23 | 9.0 | 1.0 | — | — | 16/14/20 | 20/20/22 | 30/30/32 |
| 24 | 9.0 | — | 1.0 | — | 14/12/18 | 16/16/20 | 26/26/30 |
| 25 | 9.0 | 0.5 | — | 1.0 | 10/12/16 | 10/14/16 | 16/18/26 |
| 26 | 9.0 | — | 0.5 | 1.0 | 10/10/14 | 10/12/16 | 14/16/22 |
| 27 | 9.0 | 0.25 | — | 0.5 | 10/10/12 | 12/12/16 | 18/20/26 |
| 28 | 9.0 | — | 0.25 | 0.5 | 8/8/12 | 12/12/16 | 14/18/22 |

Again, a fresh blank sample was tested (sample 22) in order to minimize bias. In table VI, the Hazen values to the left of the slash mark ("/") in are those obtained on the samples tested the same day they were prepared, the values in the center are those obtained on samples tested after being aged for two weeks at 65° C., and those to the right of the second "/" mark are those obtained by testing the samples after aging for 30 days at 65° C. In Table VI, the formulations which contained Cu 3,5-DIPS performed slightly better than the corresponding formulations which contained cupric gluconate, at all levels. Although the differences were not drastic, the synergy is still present. Both samples 26 and 28 showed identical results, indicating that superior color-change inhibition are most preferably and unexpectedly achieved by using lower amounts of additives, as in sample 28.

Thus certain derivatives of hydroxy carboxylic acids, including esters of aromatic acids and anions of alkoxy-substituted aromatic acids, function synergistically when combined at ppm levels with an acid halide to effectively inhibit the tendency of organic acid anhydride to darken when maintained at elevated temperatures. Other structurally-similar chemical compounds falling within the definition of hydroxy carboxylic acid may be combined with phthaloyl chloride in a combination as described herein include without limitation: 2-hydroxy benzoic acid; 3-hydroxy benzoic acid; 4-hydroxy benzoic acid; 2,3-di-hydroxy benzoic acid; 2,4-di-hydroxy benzoic acid; 2,5-di-hydroxy benzoic acid; 2,6-di-hydroxy benzoic acid; 3,4-di-hydroxy benzoic acid; 3,5-di-hydroxy benzoic acid; 3,6-di-hydroxy benzoic acid; 2,3,4-tri-hydroxy benzoic acid; 2,3,5-tri-hydroxy benzoic acid; 2,3,6-tri-hydroxy benzoic acid; 3,4,5-tri-hydroxy benzoic acid; 2,4,5-tri-hydroxy benzoic acid; 2,4,6-tri-hydroxy benzoic acid; the mono and polyhydroxy derivatives of carboxylic acids of naphthalene and anthracene, and all salts or esters of any of the aforesaid, including those in which the hydrogen atom of at least one hydrogen atom of a hydroxy group on the molecule is replaced by an alkyl group (thus forming an alkoxy group), straight chain or branched, wherein the alkoxy group comprises between 1 and 12 carbon atoms per alkoxy group; or combinations of any of the aforesaid, as in the case when Cu (II) 3,5-DIPS is combined with n-propyl gallate.

Other structurally-similar chemical compounds falling within the definition of hydroxy carboxylic acid may be combined with phthaloyl chloride in a combination as described herein include without limitation derivatives of the aromatic di-acids phthalic acid, terphthalic acid, and isopthlalic acid, including without limitation 3-hydroxy phthalic acid, 4-hydroxy phthalic acid, 5-hydroxy phthalic acid 3,4-dihydroxy phthalic acid, 3,5-dihydroxy phthalic acid; 3,6-dihydroxy phthalic acid; 4,5-dihydroxy phthalic acid, 3,4,5-trihydroxy phthalic acid; 3,4,6-trihydroxy phthalic acid, 2-hydroxyisophthalic acid, 2,4-dihydroxyisophthalic acid, 2,5-dihydroxyiso phthalic acid, 4,5-dihydroxyisophthalic acid, 4,6-dihydroxyisophthalic acid, 2,4,5-trihydroxyiso phthalic acid, 4,5,6-trihydroxyphthalic acid, 2-hydroxy terphthalic acid, 2,3-dihydroxyterphthalic acid, 2,5-dihydroxyterphthalic acid, 2,6-dihydroxyterphthalic acid, 2,3,5-trihydroxy terphthalic acid, and all salts or esters of any of the aforesaid, including those in which the hydrogen atom of at least one hydrogen atom of a hydroxy group on the molecule is replaced by an alkyl group (thus forming an alkoxy group), straight chain or branched, wherein the alkoxy group comprises between 1 and 12 carbon atoms per alkoxy group; or combinations of any of the aforesaid, as in the case when Cu (II) 3,5-DIPS is combined with n-propyl gallate.

In cases where anionic salts of aromatic acids of the type set forth above are utilized in combination with other species according to this invention, any cationic species may be employed as the charge-balance agent for the anion, provided no deleterious effects to the color stabilization result. In general for this to be true, the compound as a whole must be soluble in the ppm concentration ranges used. For purposes of the instant invention and the appended claims, the words "cationic species" include without limitation metals and all other atoms capable of carrying a positive charge, including the alkali metals, alkaline earth metals, transition metals of groups IIIB, IVB, VB, VIB, VIIB, VIIIB, IXB, and XB of the periodic table of the elements (especially di-valent, late transition metals such as copper and zinc), the lanthanides, the actinides, Group IIIA metals, positively charged organic species, and positively charged chemical species from or which include atoms of Groups IV and V of the periodic table of elements, including ammonium, phosphonium and arsonium, substituted or unsubstituted.

One concern for manufacturers and users of organic anhydrides which are commonly maintained above ambient temperatures is the tendency of the materials to discolor over their long-term storage. To determine whether any detrimental effects are observable with respect to stabilized samples of MAA and to re-demonstrate that long-term synergy does in fact exist with respect to the combinations of this invention, heat stress tests were performed and Hazen value data gathered on samples of MAA as outlined in Table VII below:

TABLE VII

| Sample Number | phthaloyl chloride (ppm) | Cu(II) gluconate (ppm) | n-PG (ppm) | Initial APHA | 140° C. 2 hours | 182° C. 1 hour |
|---|---|---|---|---|---|---|
| 29 | — | — | — | 10/12 | 110/150 | 400/>500 |
| 30 | — | 0.5 | — | 10/12 | 28/20 | 250/300 |
| 31 | — | 0.5 | 0.5 | 12/14 | 24/16 | 230/70 |
| 32 | 12 | 0.5 | 0.5 | 10/12 | 18/16 | 50/32 |
| 33 | 12 | 0.5 | — | 12/14 | 16/16 | 50/30 |
| 34 | 12 | — | — | 8/12 | 28/24 | 230/450 |

The Hazen value data to the left of the slash marks in the columns of table VII were obtained immediately after sample preparation, while those to the right of the slash marks were obtained following one week of being kept molten at 65° C. These data show that no negative effects were observed over the test period, but rather showed some unexpected improvement over time for samples containing cupric gluconate combined with either phthaloyl chloride or n-PG, thus evidencing the long-term stability of the discovered synergy.

Another concern relative to the manufacture and use of organic acid anhydrides which are normally solid at ambient temperatures and must hence be handled in a molten state is what effect, if any, exists owing to the repeated passing of the material between the liquid and solid states. To answer this question, the MAA compositions set forth in Table VIII were prepared, and heat stress tests performed thereon:

TABLE VIII remelt test values of color-stabilized MAA

| Sample Number | phthaloyl chloride (ppm) | Cu(II) gluconate (ppm) | n-PG (ppm) | Initial APHA | 140° C. 2 hours | 182° C. 1 hour |
|---|---|---|---|---|---|---|
| 35 | 9.0 | — | — | 8/14 | 14/16 | >70/110 |
| 36 | 9.0 | 0.5 | — | 10/20 | 14/26 | 26/40 |
| 37 | 9.0 | 0.25 | — | 10/16 | 16/22 | 26/34 |
| 38 | 9.0 | 0.5 | 1.0 | 8/24 | 14/34 | 20/>50 |
| 39 | 9.0 | 0.25 | 0.5 | 8/16 | 14/24 | 22/31 |

The values table VIII were obtained by identical methods as employed earlier. The first Hazen value in each column was obtained on the samples one day after their preparation, following their overnight storage at 65° C. After conducting the initial tests, the samples were stored at 65° C. for two weeks, then solidified by storage at ambient temperatures for one week, and finally re-melted by replacement in a 65° C. environment to effect melting at least 12 hours before the tests were run. As the data show, there seems to be a slight increase in the Hazen values obtained. However, this degree of increase is not sufficient to effect the stability of the material to the point where such material is not more desirable than what is currently available in the art.

Since commercial organic anhydrides are usually found to contain a small amount of their corresponding acid (typically not more than about 0.10%) after being stored over time, another question which arises is whether the presence of normal amounts of the corresponding acid is detrimental to the beneficial effects of the disclosed combinations taught herein. To answer this question, samples of MAA were prepared in accordance with the compositions set forth in table IX below, some of which contain free maleic acid and some of which do not, with heat stress tests conducted thereon after storage at 65° C. for 6 days. In table IX, the values obtained on the freshly prepared samples appear to the left of the slash ("/"), while the values obtained after storage at 65° C. for 6 days are set forth after the slash mark, thus:

TABLE IX effect of free maleic acid on MAA stabilized according to the invention.

| Sample Number | phthaloyl chloride (ppm) | Cu(II) gluconate (ppm) | n-PG (ppm) | maleic acid (ppm) | Initial APHA | 140° C. 2 hours | 182° C. 1 hour |
|---|---|---|---|---|---|---|---|
| 40 | 0 | 0 | 0 | 0 | 8/22 | 140/150 | >500/500 |
| 41 | 0 | 0.5 | 0.5 | 0 | 10/10 | 16/60 | 450/200 |
| 42 | 0 | 0.25 | 0.25 | 0 | 8/10 | 32/130 | 400/350 |
| 43 | 12 | 0.5 | 0.5 | 0 | 10/10 | 12/14 | 50/20 |
| 44 | 12 | 0.25 | 0.25 | 0 | 10/8 | 14/12 | >50/22 |
| 45 | 12 | 0 | 0 | 1000 | 8/8 | 12/14 | >50/80 |
| 46 | 12 | 0.5 | 0.5 | 1000 | 8/8 | 12/14 | 18/— |
| 47 | 12 | 0.25 | 0.25 | 1000 | 8/8 | 12/12 | 18/— |

In addition to showing no ill effects due to the presence of normal quantities of free organic acid in anhydride stabilized according to this invention, the data in table IX, and particularly samples 41–45, reaffirm the necessity of both the acid halide and the hydroxy acid derivative for the display of synergistic stabilization effects.

A preferred embodiment of the invention includes the addition of part per million levels of a salt of a second transition metal other than copper to maleic anhydride which contains part per million levels of phthaloyl chloride, cupric gluconate, and n-propyl gallate. Although the salt of the second transition metal other than copper may comprise any transition metal in a compound with any anion set forth or described in this specification or the appended claims, it is preferable that the second transition metal is a zinc salt, with zinc chloride being most preferred. The following compositions and test results illustrate the efficacy of zinc salts as optional additives in compositions according to the invention:

TABLE X

Zinc-bearing compositions according to the invention

| Sample Number | Phthaloyl chloride (ppm) | Cu(II) gluconate (ppm) | n-PG (ppm) | Zinc salts (ppm) chloride | Zinc salts (ppm) gluconate | Initial APHA | 182° C. 1 hour | 182° C. 2 hours |
|---|---|---|---|---|---|---|---|---|
| 48 | 9.0 | 0.5 | 0.5 | 0 | 0.5 | 8 | 18 | — |
| 49 | 9.0 | 0.25 | 0.25 | 0 | 0.25 | 8 | 22 | — |
| 50 | 9.0 | 0.5 | 0.5 | 0 | 0.5 | 8 | 30 | 70 |
| 51 | 9.0 | 0.5 | 0.5 | 0 | 0.5 | 12 | 24 | 60 |
| 52 | 9.0 | 0.5 | 0.5 | 0.5 | 0 | 12 | 24 | >50 |

To verify that the compositions taught herein are stable over long periods with respect to their inhibition to color changes, further compositions of MAA were prepared and evaluated. The data in Table X show the stability of a sample kept at 65° C. (samples 53, 55, and 57) versus samples stored at ambient temperatures in the solid state and melted by placing in a 65° C. oven just prior to testing (samples 54, 56, 58). APHA values shown in the table are for successive tests run one week apart. Thus, for example, the data listed under the heading "182° C., 1 hour" for sample 53 show the Hazen values for the sample after one week of aging to be 14, after two weeks to be 16, after 3 weeks to be 16, and after 4 weeks to be 18.

TABLE XI extended time heat stability tests on re-melted samples versus samples maintained in the molten state.

| Sample No. | Phthaloyl Chloride (ppm) | Cu(II) gluconate (ppm) | n-PG (ppm) | Initial APHA | 140° C. 2 hours | 182° C. 1 hour |
|---|---|---|---|---|---|---|
| 53 | 9.0 | 0.25 | 0.25 | 10/10/10/10 | 12/12/12/14 | 14/16/16/18 |
| 54 | 9.0 | 0.25 | 0.25 | 12/14/12/12 | 18/20/22/24 | 30/32/34/36 |
| 55 | 9.0 | 0 | 0 | 8/10/14/14 | 16/18/18/22 | 230/180/450/160 |
| 56 | 9.0 | 0 | 0 | 10/10/16/14 | 20/60/26/22 | 400/400/500/325 |
| 57 | 9.0 | 0.5 | 0.5 | 10/10/16/16 | 12/14/16/18 | 18/22/22/26 |
| 58 | 9.0 | 0.5 | 0.5 | 12/12/16/16 | 22/22/28/28 | 36/36/40/>40 |
| 59 | 9.0 | 0.5 | 0.5 | 10/10/10/12/14/14 | 14/14/14/22/24/22 | 16/18/18/32/40/36 |

Sample 59 shows results for a sample of material of the composition shown which was re-melted successively. The first APHA values are for the sample as prepared and each succeeding value in each column represents APHA values for the sample after being re-melted on the first, second, seventh, eighth, and ninth days following, respectively.

Overall, the data of Table XI show that the compositions of anhydride stabilized according to the invention are in fact stable over extended periods of time normally encountered during the typical time frame associated with the manufacture, storage, and use of MAA.

While the present invention has been described as an anhydride product that is formed from components comprising an organic acid anhydride; an acid halide of a carboxylic acid; and at least one derivative of a hydroxy carboxylic acid, there may be components present other than those specified, provided any other components present do not exert a significant deleterious effect on the high temperature color stability of the anhydride product, nor interact undesirably with the reactivity of the anhydride product in an end use selected by a consumer of the anhydride product.

Although a myriad of combinations of additive components described above is possible using the teachings herein, the most preferred stabilized organic acid anhydrides according to this invention comprises that exemplified by maleic acid anhydride which contains 12.0 ppm of phthaloyl chloride, 0.5 ppm of cupric gluconate, 0.5 ppm of zinc chloride, and 0.5 ppm of propyl gallate, all preferably added to molten maleic anhydride with sufficient agitation to form a homogenous mixture. However, equivalent alterations of and modifications to the embodiments set forth herein including the preferable and the most preferred embodiment are destined to become apparent to those of ordinary skill in this art upon reading and thoroughly understanding this specification and the appended claims. The present invention, embraces all such modifications and alterations, and is limited only by the scope of the claims which follow.

I claim:

1. A process for stabilizing organic acid anhydrides against color changes which comprises the steps of:
    a) providing an organic acid anhydride;
    b) contacting said anhydride with an acid halide of a carboxylic acid; and
    c) contacting said anhydride with a derivative of a hydroxy carboxylic acid.

2. The process according to claim 1 wherein said anhydride is maleic acid anhydride.

3. The process according to claim 1 wherein the acid halide is selected from the group consisting of formyl chloride, acetyl chloride, phthaloyl chloride, succinyl chloride, and maleyl chloride.

4. The process according to claim 1 wherein said derivative of a hydroxy carboxylic acid comprises at least one of:

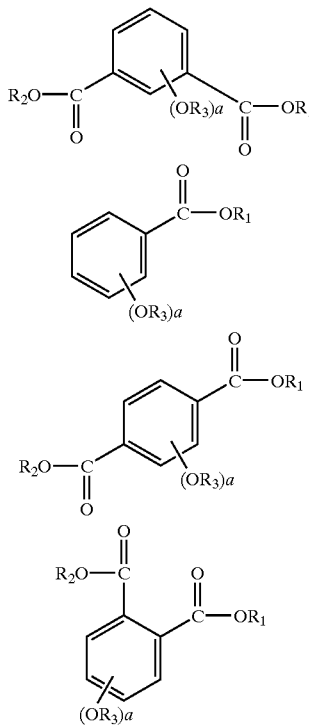

wherein $R_1$, $R_2$ are each independently selected from the group consisting of a cationic species; hydrogen; $C_1$ through $C_{12}$ straight-chain, branched, or cyclic alkyl; $C_1$ through $C_{12}$ straight-chain, branched, or cyclic alkenyl; substituted or unsubstituted phenyl; and $R_3$ is independently selected from the group consisting of a cationic species; hydrogen; $C_1$ through $C_{12}$ straight-chain, branched, or cyclic alkyl; $C_1$ through $C_{12}$ straight-chain, branched, or cyclic alkenyl; substituted or unsubstituted phenyl; and a is any of the integers 1, 2, 3, or 4, and including all isomers thereof.

5. The process of claim 1 in which said derivative of a hydroxy carboxylic acid is a derivative of a hydroxy carboxylic acid which is non-aromatic in character.

6. The process of claim 1 in which said derivative of a hydroxy carboxylic acid is a derivative of a hydroxy carboxylic acid selected from the group consisting of: gluconic, glucoheptonic, hydroxyacetic, hydroxyproprionic, and hydroxybutyric acids.

7. A process for stabilizing organic acid anhydrides against color changes which comprises the steps of:

a) providing an organic acid anhydride in the liquid state;

b) causing an acid halide of a carboxylic acid to exist within said anhydride in the liquid state to form a first mixture;

c) causing at least one derivative of a hydroxy carboxylic acid to exist within said first mixture so as to form a final mixture; and d) effecting agitation sufficient to render said final mixture at least reasonably homogeneous.

8. A process according to claim 7 further comprising the step of:

e) maintaining said organic acid anhydride in its liquid state.

9. A process according to claim 7 further comprising the step of:

e) causing said organic acid anhydride to undergo a phase change from the liquid state to the solid state.

10. A process according to claim 9 further comprising the step of:

f) causing said organic anhydride to undergo a subsequent phase change from the solid state to the liquid state.

* * * * *